United States Patent [19]

Larkins, Jr.

[11] Patent Number: 4,886,905
[45] Date of Patent: Dec. 12, 1989

[54] PREPARATION OF ETHYL ACETATE

[75] Inventor: Thomas H. Larkins, Jr., Kingsport, Tenn.

[73] Assignee: Eastman Kodak Company, Rochester, N.Y.

[21] Appl. No.: 497,477

[22] Filed: May 23, 1983

Related U.S. Application Data

[63] Continuation of Ser. No. 230,172, Jan. 30, 1981, abandoned.

[51] Int. Cl.$^4$ .................. C07C 67/00; C07C 67/297; C07C 69/14
[52] U.S. Cl. .................... 560/265; 560/232; 560/263; 562/607
[58] Field of Search .............. 560/265, 263; 562/607

[56] References Cited

U.S. PATENT DOCUMENTS 3,579,566  5/1971  Fenton .................. 560/263
4,221,918  9/1980  Suzuki .................. 560/263

FOREIGN PATENT DOCUMENTS 1538782  1/1979  United Kingdom ........... 560/232

Primary Examiner—Vivian Garner
Attorney, Agent, or Firm—J. Frederick Thomsen; Daniel B. Reece, III

[57] ABSTRACT

Process for the preparation of ethylidene diacetate and/or ethyl acetate by hydrogenating acetic anhydride in the presence of a homogeneous ruthenium catalyst, methyl iodide and, optionally, lithium iodide. The process can also be utilized to hydrogenate mixtures of acetic anhydride and ethylidene diacetate to produce ethyl acetate.

4 Claims, No Drawings

PREPARATION OF ETHYL ACETATE

This is a continuation of application Ser. No. 230,172 filed Jan. 30, 1981, now abandoned.

This invention relates to a novel process for the preparation of ethylidene diacetate and ethyl acetate by hydrogenating acetic anhydride. The invention also relates to a novel process for hydrogenating mixtures of acetic anhydride and ethylidene diacetate to obtain ethyl acetate.

An economically advantageous process for the preparation of acetic anhydride by the carbonylation of methyl acetate has been reported in the patent literature. See, for example, Belgian Patent 819,455, British Published Patent Application 2,013,184, Japanese Published Patent Appliccations 75-47921 and 75-47922 and U. S. Paents 3,9227,078 and 4,046,807. Not onlyis acetic anhydride itself an important chemical, for example as an acetylating agent in the manufacture of cellulose acetate and other esters, but it can be converted to ethylidene diacetate and ethyl acetate. The ethylidene diacetate can be converted to vinyl acetate which, along with ethyl acetate, are derived primarily from petroleum. Very little prior art exists concerning the hydrogenation of acetic anhydride. The hydrogenation ofo acetic anhydride to ethylidene diacetate and acetic acid with a catalyst consisting of a Group VIII noble metal and a hiphyllic ligand selected from the group consisting of trihydrocarbyl phosphines, arsines, and stibines is disclosed in U. S. Patent 3,579,566. With these catalysts the reaction rate was slow. Depending upon the reaction conditions and catalyst used, ethyl acetate and acetic acid were produced, along with the desired ethylidene diacetate product. The co-production of acetic anhydride nd ethylidene diacetate by the carbonylation of methyl acetate in the presence of hydrogen, a Group VIII noble metal catalyst and methyl iodide is disclosed in Belgian Paent 839,321. The preparation of ethylidene diacetate from acetic anhydride using a supported palladium catalyst in the presence of a strong acid, i.e., HCl, HF, or methane sulfonic acid, is disclosed in Belgian Patent 879,178. When HCl was the acid used, large amounts of 1-chloroethylacetate were produced along with the desired ethylidene diacetate and aceticc acid products. The hydrogenation of acetic anhydride to ethyl acetate with Ru(Xhd 2)(PR$_3$)$_3$ catalyst where X is a halogen or lower alkyl and PR$_3$ is an alkyl or aryl phosphine is described in U. S. Paten 3,957,827. B er., 63B, 796 (1930) discloses the hydrogenation of acetic anhydride to ethyl acetate with a palladium black catalyst. Addition of HCl promoted the hydrogenation reaction.

The process of this invention comprises hydrogenating at elevated pressure and temperature acetic anhydride in the presence of a catalytic amount of a homogeneous ruthenium compound, methyl iodide and, optionally, lithium iodide. Depending upon how much methyl iodide and lithium iodide are employed, the process can be utilized to produce all or essentially all ethylidene diacetate, all or essentially all ethyl acetate or a mixture of the two in good to excellent space-time yields. The process also can be used to convert mixtures of acetic anhydride and ethylidene diacetate, resulting from the carbonylation of methyl acetate in the presence of hydrogen, to ethyl acetate. The feed to the hydrogenation reactor can, if desired, contain, in addition to acetic anhydride and/or ethylidene diacetate, an inert solvent such as acetic acid.

The reactions involved in the process are:

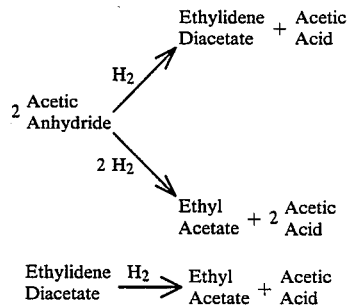

The co-produc acetic acid may be converted to methyl acetate and used in the production of acetic anhydride.

The concentration of the ruthenium can be varied substantially depending on such factors as the temperature and pressure employed, the space-time yield desired, etc. Generally, ruthenium (as Ru) concentrations in the range of about 100 to 2500 ppm, based on the acetic anhydride and/or ethylidene diacetate fed, will give good results when using appropriate pressures and temperatures. Ruthenium concentrations (same basis) of about 500 to 1000 ppm will most often be used. The particular ruthenium compound charged to the hydrogenation reactor is not critical so long as it is soluble in the reaction medium or results in the formation of a soluble form of ruthenium, i.e. a homogenous catalyst. Examples of suitable ruthenium compounds include ruthenium chloride, ruthenium acetate, ruthenium iodide, etc.

The hydrogenation-effective temperature and pressures employed in the process of this invention also can be varied substantially. Not only are temperature and pressure interdependent with respect to reaction rate but each also is dependent upon catalyst concentrations. Temperatures in the range of about 125 to 250° C. may be used although at the higher temperatures tar formation may be a problem, especially in continuous operations. The preferred temperatures are from about 160 to 210° C., especially 185 to 210° C. Pressures (total reaction pressure) in the range of about 250 to 2500 psig may be used, although pressures of about 500 to 2200 psig, especially about 1000 to 2000 psig, are preferred.

The amount of methyl iodide employed depends on the particular product or co-products that are desired, the temperature and, to a lesser degree, the pressure employed in the hydrogenation process. When it is desired to hydrogenate acetic anhydride to essentially all ethylidene diacetate, the amount of methyl iodide employed should be in the range of about 3 to 15 weight percent based on the acetic anhydride fed. The use of methyl iodide alone in the lower part of the range generally will require the use of higher temperatures, e.g. 200° C. or above. The presence of lithium iodide in a concentrataion of about 0.2 to 2.0, preferably 0.5 to 1.5, weight percent based on the weight of the acetic anhydride, usually improves the rate of ethylidene diacetate formation depending on temperature. The lithium iodide may be fed as such or it may be generated in the reaction mixture from other lithium compounds such as lithium hydroxide, lithium carbonate or lithium acetate.

In hydrogenating acetic anhydride to essentially all ethyl acetate the amount of methyl iodide fed should be about 1.5 weight percent and under most conditions about 0.25 to 1 weight percent based on the weight of the reactant(s), i.e., acetic anhydide and, when present ethylidene diacetate. To obtain good reaction rates for the production of ethyl acetate, very little, e.g. up to about 0.1 weight percent of lithium iodide, and preferably no lithium iodide is present. When it is desired to produce significant amounts of ethylidene diacetate and ethyl acetate, e.g. in weight ratios of or between about 2:1 to 1:2, the amount of methyl iodide normally charged is about 7.5 to 25 weight percent while the amount of lithium iodide should be in the range of about 0.5 to 1.5 weight percent.

The amounts of methyl iodide and lithium iodide that may be used to convert mixtures of acetic anhydride and ethylidene diacetate to essentially all ethyl acetate can be varied considerably depending on such variables as the amounts of each reactant in the mixture, the temperature employed and the hydrogen pressure. Generally, for mixtures of acetic anhydride and ethylidene diacetate in a weight ratio of about 3:1 to 1:3, the amount of methyl iodide fed should be in the range of about 0.25 to 5 weight percent based on the weight of the reactants. In hydrogenating the mixture to essentially all ethyl acetate, very little, up to 0.1 weight percent of lithium iodide, and preferably no, lithium needs to be present.

The process of the invention may be carried out as a batch operation or, more suitably, as a continuous process wherein acetic anhydride and/or ethylidene diacetate are continuously fed to a hydrogenation reactor and reaction mixture containing the desired product or products is continuously removed. Unreacted materials and co-product acetic acid may be removed from the reactor take-off, for example, in a distillation train, and recycled, along with any catalyst and iodides present, to the reactor.

The process of the invention is further illustrated by the following examples.

EXAMPLES 1-25

Acetic anhydride (100 g.) was hydrogenated for 30 minutes in the presence of ruthenium charged as 0.25 g. ruthenium chloride using different temperatures and total autoclave pressures and varying amounts of methyl iodide and lithium iodide. The acetic anhydride, ruthenium chloride, methyl iodide and lithium iodide (when used) were loaded into a 300 ml. Hastalloy B autoclave designed to operate in a rocking mode. The autoclave was purged with 100 psig hydrogen gas pressure at room temperature and then the gas was vented. The autoclave internal pressure was increased to 10 psig by adding hydrogen gas at room temperature. The autoclave was sealed and heated and rocked until reaction temperature was reached, at which time additional hydrogen gas was added to increase the autoclave internal pressure to the predetermined value. The time at which the autoclave internal pressure reached the predetermined value was taken as the start of the 30-minute reaction time. Reactor pressure was maintained at the preset value during the experiment by adding hydrogen gas at the same rate at which it was consumed by the reactants. When the predetermined reaction time was completed, the autoclave was cooled by a stream of cold air. After the gas was vented from the autoclave, the reaction product was analyzed by gas chromatographic methods.

Table I shows the temperature (° C.) and pressure (psig) used, the amounts of methyl and lithium iodide ($CH_3I$, $LiI$, g.) charged, the amounts (in moles) of ethyl cetate (EA), acetic acid (HOAc) and ethylidene diacetate (EDA) produced, he amount of acetic anhydride ($Ac_2O$, in moles) recovered and the space-time yields (STY, in grams/liter-hour) for ethylidene diacetate and ethyl acetate.

TABLE I

| Example | Temp. | Pressure | LiI | MeI | EA | HOAc | $Ac_2O$ | EDA | EDA STY | EA STY |
|---|---|---|---|---|---|---|---|---|---|---|
| 1 | 200 | 500 | — | — | — | 0.344 | 0.718 | 0.031 | 91 | — |
| 2 | 200 | 500 | — | 0.35 | 0.259 | 1.020 | — | — | — | 456 |
| 3 | 200 | 500 | — | 0.50 | 0.375 | 1.20 | 0.032 | 0.003 | 9 | 660 |
| 4 | 160 | 2000 | — | 0.50 | 0.388 | 1.26 | — | 0.01 | 29 | 682 |
| 5 | 200 | 2000 | — | 0.50 | 0.443 | 1.10 | — | — | — | 780 |
| 6 | 210 | 1000 | — | 1.0 | 0.390 | 1.21 | 0.034 | — | — | 686 |
| 7 | 170 | 2000 | — | 1.0 | 0.240 | 0.88 | 0.09 | 0.101 | 295 | 419 |
| 8 | 210 | 2000 | — | 1.0 | 0.340 | 1.17 | 0.037 | — | — | 600 |
| 9 | 170 | 1000 | — | 1.0 | 0.251 | 1.26 | 0.041 | 0.015 | 44 | 442 |
| 10 | 190 | 1500 | — | 5.0 | 0.004 | 0.272 | 0.724 | 0.068 | 198 | 7 |
| 11 | 170 | 1000 | — | 9.0 | 0.014 | 0.563 | 0.408 | 0.161 | 470 | 25 |
| 12 | 210 | 1000 | — | 9.0 | 0.001 | 0.362 | 0.722 | 0.055 | 161 | — |
| 13 | 170 | 2000 | — | 9.0 | — | 0.308 | 0.498 | 0.205 | 600 | — |
| 14 | 210 | 2000 | — | 9.0 | 0.017 | 0.602 | 0.476 | 0.099 | 289 | 30 |
| 15 | 190 | 2000 | 1.0 | 9.0 | 0.002 | 0.268 | 0.614 | 0.169 | 493 | 4 |
| 16 | 175 | 2000 | 1.5 | 13.0 | 0.012 | 0.135 | 0.796 | 0.050 | 146 | 21 |
| 17 | 175 | 2000 | 0.5 | 5.0 | 0.008 | 0.066 | 0.808 | 0.039 | 114 | 14 |
| 18 | 205 | 2000 | 0.5 | 5.0 | 0.018 | 0.457 | 0.250 | 0.294 | 858 | 32 |
| 19 | 175 | 2000 | 1.5 | 13.0 | 0.007 | 0.175 | 0.641 | 0.126 | 368 | 12 |
| 20 | 205 | 2000 | 0.5 | 13.0 | 0.018 | 0.643 | 0.022 | 0.365 | 1066 | 32 |
| 21 | 205 | 2000 | 1.5 | 5.0 | 0.016 | 0.301 | 0.502 | 0.174 | 508 | 28 |
| 22 | 205 | 2000 | 1.5 | 13.0 | 0.006 | 0.432 | 0.347 | 0.255 | 745 | 10 |
| 23 | 175 | 2000 | 0.5 | 5.0 | 0.003 | 0.105 | 0.866 | 0.037 | 114 | 5 |
| 24 | 190 | 2000 | 0.1 | 21.0 | 0.165 | 0.98 | 0.064 | 0.131 | 382 | 290 |
| 25 | 190 | 2000 | 0.1 | 9.0 | 0.181 | 0.735 | 0.078 | 0.154 | 450 | 318 |

EXAMPLE 26

Ethylidene diacetate (100 g.) was hydrogenated at 190° C. for 1 hour at a total autoclave pressure of 100 psig in the presence of 0.25 g. ruthenium chloride and 9.0 g. methyl iodide according to the procedure employed in the previous examples. Ethyl acetate (0.578 moles) was recovered in a theoretical yield of about 85% and a space-time yield of about 500 g./l.-hr.

EXAMPLES 27-35

A mixture of acetic anhydride and ethylidene diacetate (50 g. of each) was hydrogenated in the presence of ruthenium charged as 0.25 ruthenium chloride using different temperatures and pressures and varying amounts of methyl iodide. No lithium iodide was used in these runs. The acetic anhydride, ethylidene diacetate, ruthenium chloride and methyl iodide were loaded into a 300 ml. Hastalloy B autoclave designed to operate in a rocking mode. The autoclave was purged with hydrogen at room temperature and then a predetermined amount of hydrogen was added. The autoclave was sealed and heated and rocked until a predetermined temperature was reached and then held at that temperature for 30 minutes. No additional hydrogen was added during the reaction period. When the 30-minute reaction time was completed, the autoclave was cooled by a stream of cold air. After the gas was vented from the autoclave, the reaction product was analyzed by gas chromotographic methods.

Table II shows the temperature (° C.) used, the amounts of hydrogen ($H_2$, moles) and methyl iodide ($CH_3I$, g.) charged, the amounts (in moles) of ethyl acetate (EA) and acetic acid (HOAc) produced, the amount (in moles) of acetic anydride ($Ac_2O$) and ethylidene diacetate (EDA) produced, the amount recovered andn the percent yield and space-time yield (STY, in grams/liter-hour) for ethyl acetate produced.

TABLE II

| Example | Temp. | $H_2$ | $CH_3I$ | EA | HOAc | $Ac_2O$ | EDA | EA % Yield | EA STY |
|---------|-------|-------|---------|-------|-------|---------|-------|------------|--------|
| 27 | 175 | 1.0 | 1.0 | 0.256 | 0.763 | 0.091 | 0.095 | 57.3 | 451 |
| 28 | 160 | 0.5 | 1.75 | 0.052 | 0.145 | 0.266 | 0.372 | 63.4 | 92 |
| 29 | 160 | 1.5 | 0.25 | 0.137 | 0.340 | 0.176 | 0.303 | 81.1 | 241 |
| 30 | 190 | 0.5 | 0.25 | 0.123 | 0.367 | 0.137 | 0.301 | 56.4 | 216 |
| 31 | 160 | 1.5 | 1.75 | 0.265 | 1.210 | 0.055 | 0.017 | 48.8 | 466 |
| 32 | 190 | 0.5 | 1.75 | 0.069 | 0.235 | 0.218 | 0.340 | 50.0 | 121 |
| 33 | 190 | 1.5 | 0.25 | 0.196 | 0.750 | 0.141 | 0.154 | 54.1 | 271 |
| 34 | 190 | 1.5 | 1.75 | 0.323 | 1.320 | 0.016 | — | 55.8 | 568 |
| 35 | 160 | 0.5 | 0.25 | 0.109 | 0.427 | 0.161 | 0.314 | 56.6 | 192 |

Although the invention has been described in considerable detail with particular reference to certain preferred embodiments thereof, variations and modifications can be effected within the spirit and scope of the invention.

I claim:

1. Process for the preparation of ethyl acetate which comprises hydrogenating acetic anhydride at a pressure of about 500 to 2200 psig and a temperature of about 160 to 210° C. in the presence of a catalytic amount of a homogeneous ruthenium compound in the presence of about 0.25 to 1.5 weight percent methyl iodide based on the acetic anhydride and up to about 0.1 weight perent lithium iodide based on the weight of the acetic anhydride.

2. Process according to claim 1 wherein the ruthenium concentration is about 500 to 1000 ppm based on the acetic anhydride, the pressure is about 1000 to 2000 psig, the temperature is about 185 to 210° C. and the methyl iodide present is about 0.25 to 1 weight percent.

3. Process for the preparation of ethyl acetate which comprises hydrogenating a mixture of acetic anhydride and ethylidene diacetate at a pressure of about 500 to 2200 psig and a temperature of about 160 to 210° C., in the presence of a catalytic amount of a homogeneous ruthenium compound in the presence of about 0.25 to 5.0 weight percent methyl iodide and up to about 0.1 weight percent lithium iodide, based on the weight of the acetic anhydride and ethylidene diacetate.

4. Process according to claim 3 wherein the ruthenium concentration is about 500 to 1000 ppm based on the acetic anhydride and ethylidene diacetate, the pressure is about 1000 to 2000 psig, the temperature is about 185 to 210° C. and the methyl iodide present is about 0.25 to 1.75 weight percent.

* * * * *